US008558025B2

(12) United States Patent
Gadewar

(10) Patent No.: US 8,558,025 B2
(45) Date of Patent: Oct. 15, 2013

(54) ETHYL ACETATE PRODUCTION

(75) Inventor: Sagar B Gadewar, Goleta, CA (US)

(73) Assignee: Greenyug, LLC, Santa Barbara, CA (US)

( * ) Notice: Subject to any disclaimer, the term of this patent is extended or adjusted under 35 U.S.C. 154(b) by 77 days.

(21) Appl. No.: 12/925,460

(22) Filed: Oct. 20, 2010

(65) Prior Publication Data

US 2012/0035390 A1 Feb. 9, 2012

Related U.S. Application Data

(60) Provisional application No. 61/253,349, filed on Oct. 20, 2009.

(51) Int. Cl.
*C07C 67/40* (2006.01)
(52) U.S. Cl.
USPC .......................................................... 560/239
(58) Field of Classification Search
CPC ....................................................... C07C 67/40
See application file for complete search history.

(56) References Cited

U.S. PATENT DOCUMENTS

| | | | |
|---|---|---|---|
| 3,714,236 A | 1/1973 | Wright, Jr. et al. | |
| 4,052,424 A | 10/1977 | Vanderspurt | |
| 4,220,803 A | 9/1980 | Marcinkowsky et al. | |
| 4,379,028 A | 4/1983 | Berg et al. | |
| 4,435,595 A | 3/1984 | Agreda et al. | |
| 4,440,946 A | 4/1984 | Summerville et al. | |
| 4,523,027 A | 6/1985 | Kummer et al. | |
| 4,569,726 A | 2/1986 | Berg et al. | |
| 4,996,007 A | 2/1991 | Chao et al. | |
| 5,194,675 A | 3/1993 | Joerg et al. | |
| 5,334,751 A | 8/1994 | Lemanski et al. | |
| 6,809,217 B1 | 10/2004 | Colley et al. | |
| 2009/0005588 A1* | 1/2009 | Hassan et al. | 560/232 |
| 2012/0178962 A1 | 7/2012 | Gadewar | |

FOREIGN PATENT DOCUMENTS

| | | |
|---|---|---|
| BR | 9104652 A | 4/1993 |
| EP | 0101910 A1 | 3/1984 |
| EP | 0151886 A1 | 8/1985 |
| EP | 0201105 A1 | 11/1986 |
| EP | 0331021 A1 | 9/1989 |
| FR | 2743060 A1 | 7/1997 |
| GB | 287846 | 4/1929 |
| GB | 312345 | 8/1930 |
| GB | 470773 | 8/1937 |
| JP | 59025334 A | 2/1984 |
| JP | 5186392 A | 7/1993 |
| SU | 362814 A1 | 12/1972 |

OTHER PUBLICATIONS

Filing receipt and specification for patent application entitled "Ethyl acetate production," by Sagar B. Gadewar, et al., filed Feb. 1, 2012 as U.S. Appl. No. 13/363,858.
Filing receipt and specification for provisional patent application entitled "Ethyl acetate production," by Sagar B. Gadewar, filed Oct. 20, 2009 as U.S. Appl. No. 61/253,349.
Foreign communication from a related counterpart application—International Search Report and Written Opinion, PCT/US2011/056015, May 24, 2012, 8 pages.
Inui, Kanichiro, et al., "Effective formation of ethyl acetate from ethanol over Cu—Zn—Zr—Al—O catalyst," Journal of Molecular Catalysis A: Chemical, 2004, pp. 147-156, vol. 216, Elsevier B.V.
Takeshita, Kenji, et al., "Reduced copper catalyzed conversion of primary alcohols into esters and ketones," Bulletin of the Chemical Society of Japan, 1978, pp. 2622-2627, vol. 51, No. 9.
Tsai, Reui-Chiang, et al., "Design and control of the side reactor configuration for production of ethyl acetate," Ind. Eng. Chem. Res., 2008, pp. 9472-9484, vol. 47, No. 23, American Chemical Society.
Foreign communication from a related counterpart application—International Search Report and Written Opinion, PCT/US2013/024104, May 30, 2013, 14 pages.
Inui, Kanichiro, et al., "Direct Synthesis of Ethyl Acetate, from Ethanol Carried Out under Pressure," Journal of Catalysis: 2004, pp. 207-215, vol. 212, Elsevier B.V.
Notice of Allowance dated Jun. 4, 2013 (8 pages), U.S. Appl. No. 13422,743, filed Mar. 6, 2012.
Office Action (Restriction Requirement) dated Oct. 15, 2012 (6 pages), U.S. Appl. No. 13/422,743, filed Mar. 16, 2012.
Office Action dated Jan. 10, 2013 (10 pages), U.S. Appl. No. 13/422,743, filed Mar. 16, 2012.
Santacesaria, E., et al., "Ethanol Dehydrogenation to Ethyl Acetate by Using Copper and Copper Chromite Catalysts," Chemical Engineering Journal, 2012, pp. 209-220, vol. 179, Elsevier B.V.

* cited by examiner

*Primary Examiner* — Paul A Zucker
(74) *Attorney, Agent, or Firm* — Conley Rose, PC; Rodney B. Carroll; Andrew M. Metraller

(57) ABSTRACT

A process for the production of high purity ethyl acetate from ethanol is described. The process involves reacting ethanol over a suitable catalyst in a reactive distillation column. The reactive distillation setup allows overcoming the reaction equilibrium for increased conversion of ethanol. Hydrogen is removed as the distillate and ethyl acetate is obtained as a bottoms product from the reactive distillation column. A feed of hydrogen at the bottom of the column and a suitable hydrogenation catalyst placed at the bottom of the column allows for a significant reduction of impurities such as butan-2-one, butyraldehyde in the ethyl acetate product. Adding side reactors to the reactive distillation column allows additional catalyst holdup for improved reactant conversion.

20 Claims, 8 Drawing Sheets

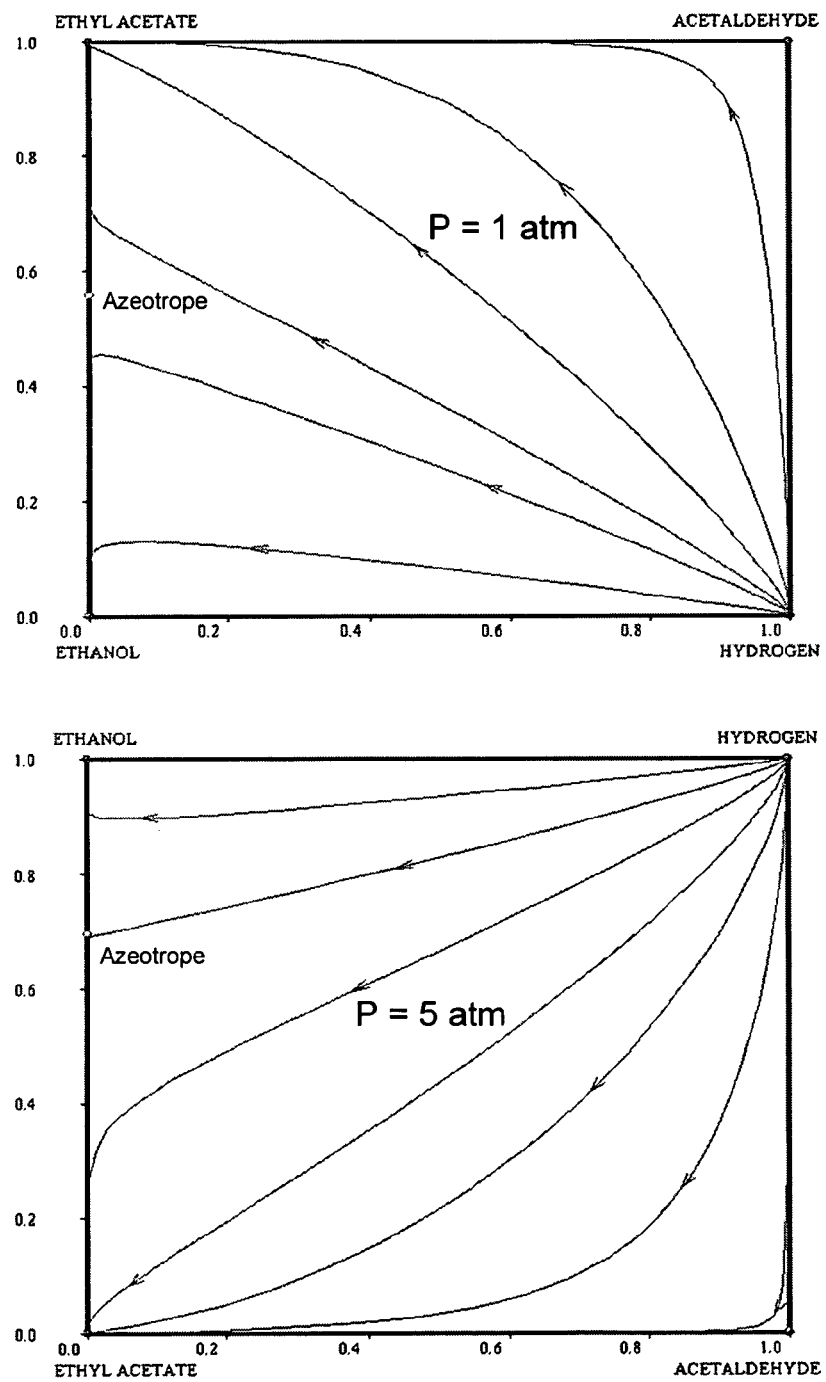
Figure 1: Reactive residue curve maps at pressures of 1 atm and 5 atm.

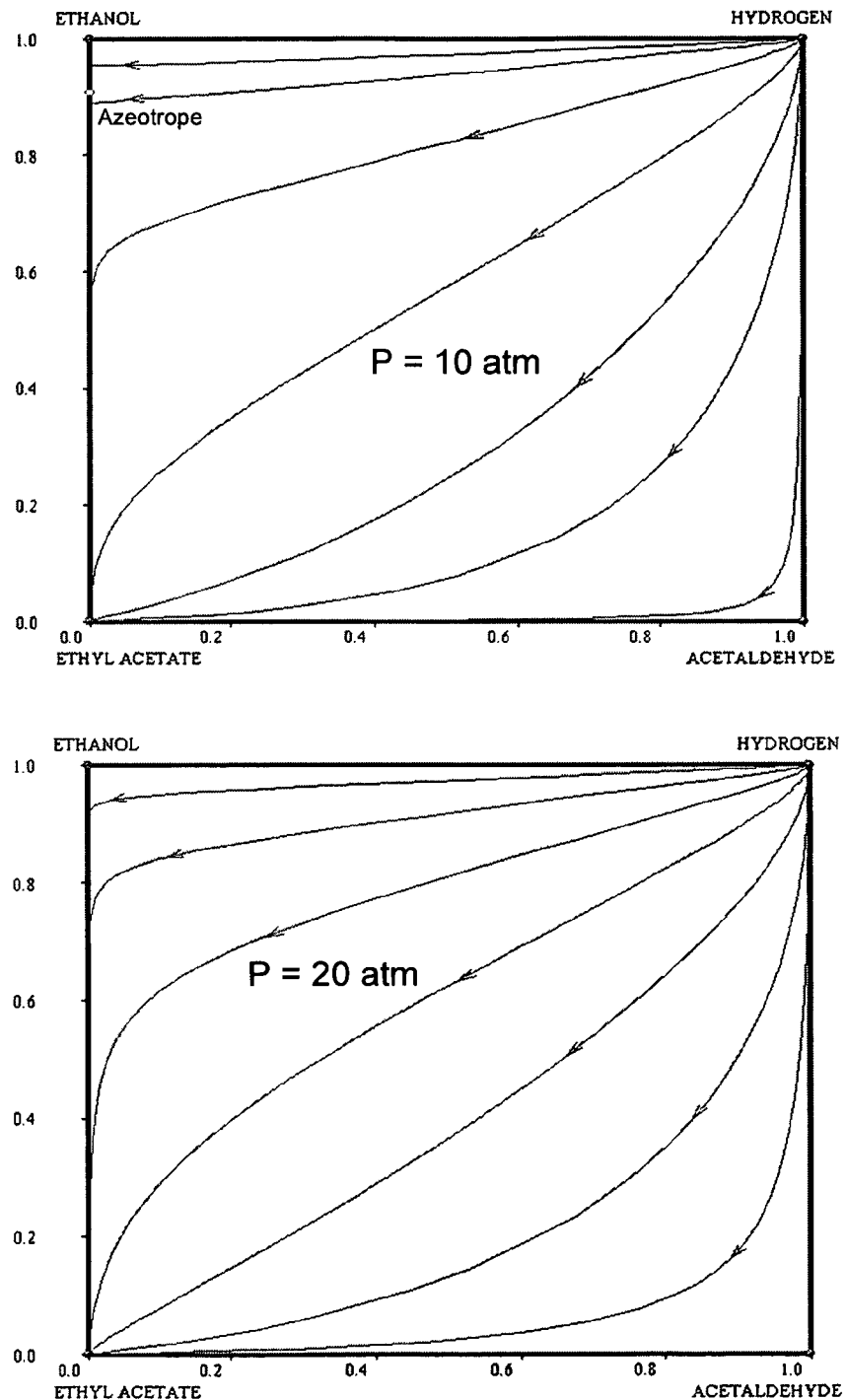
Figure 2: Reactive residue curve maps at pressures of 10 atm and 20 atm.

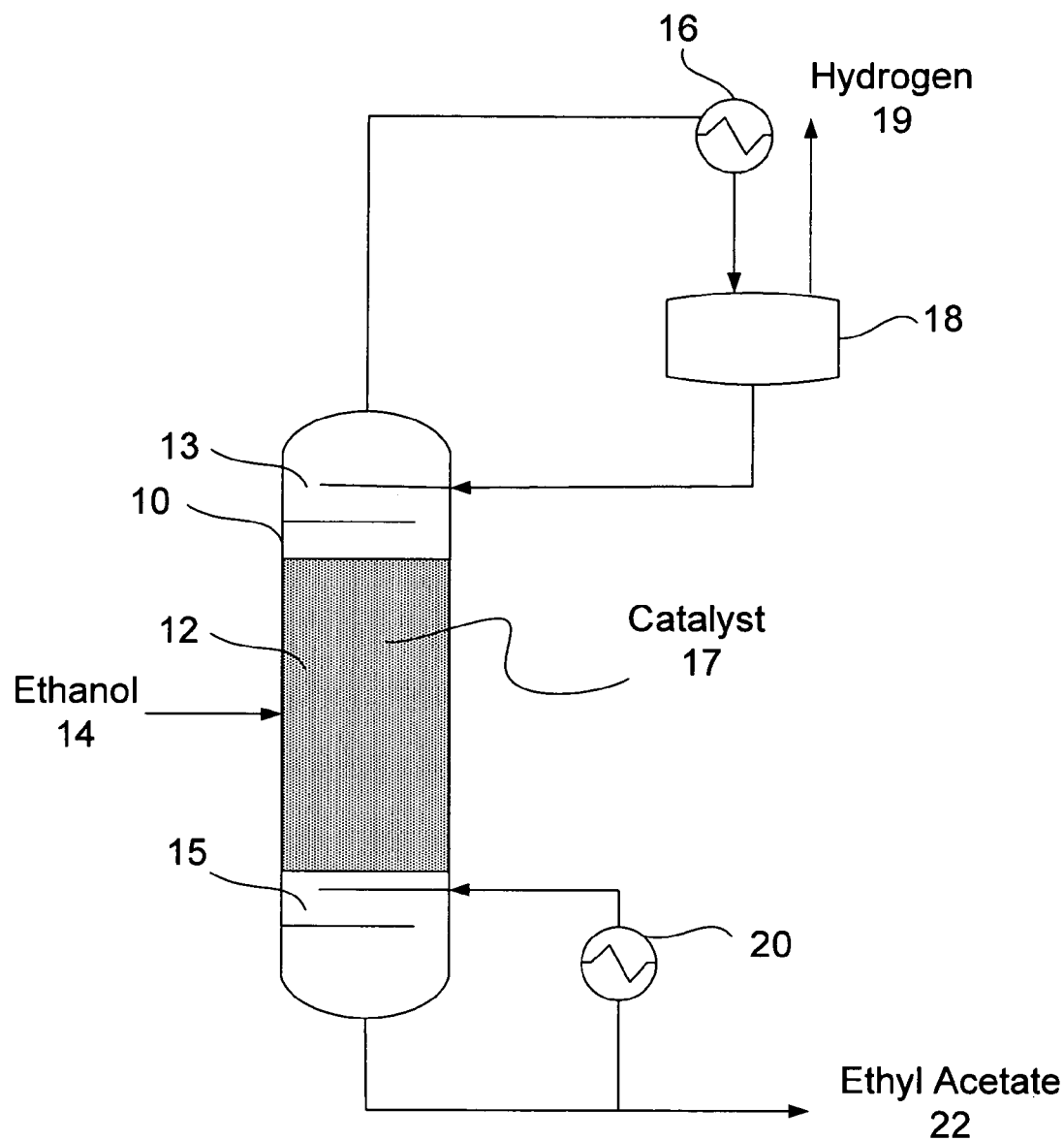
Figure 3: Single feed reactive distillation column schematic.

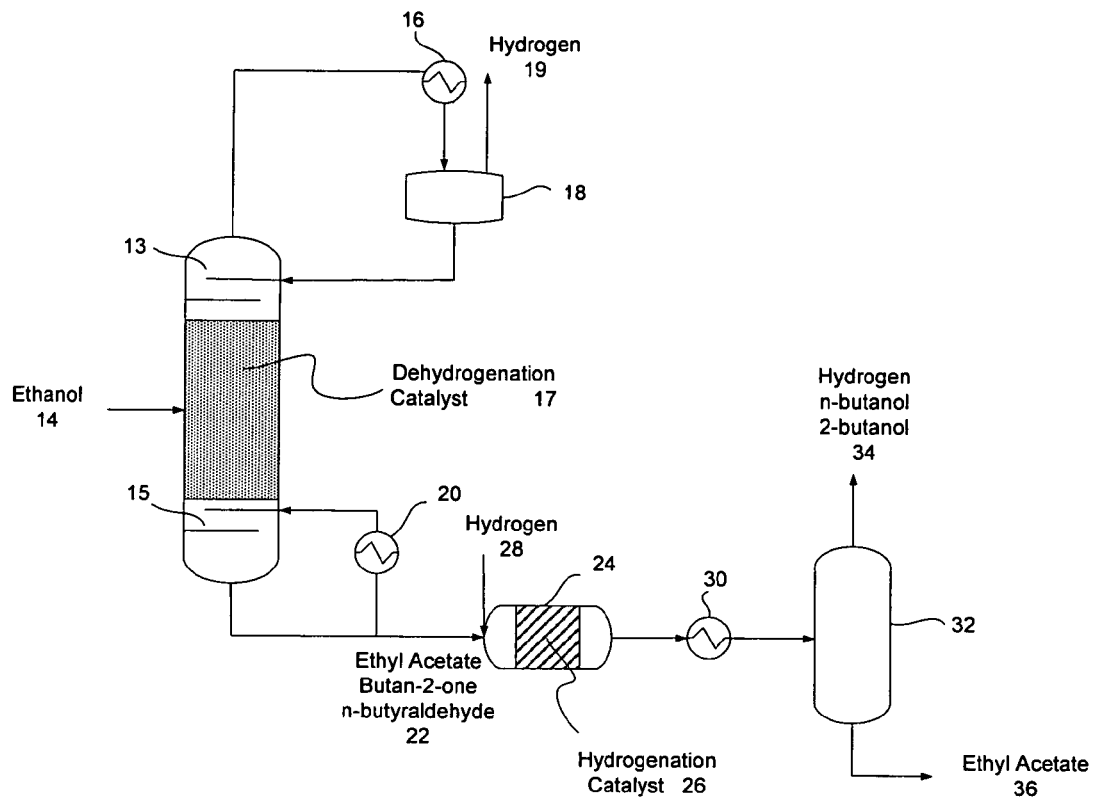
Figure 4: Schematic for a reactive distillation system with subsequent product hydrogenation.

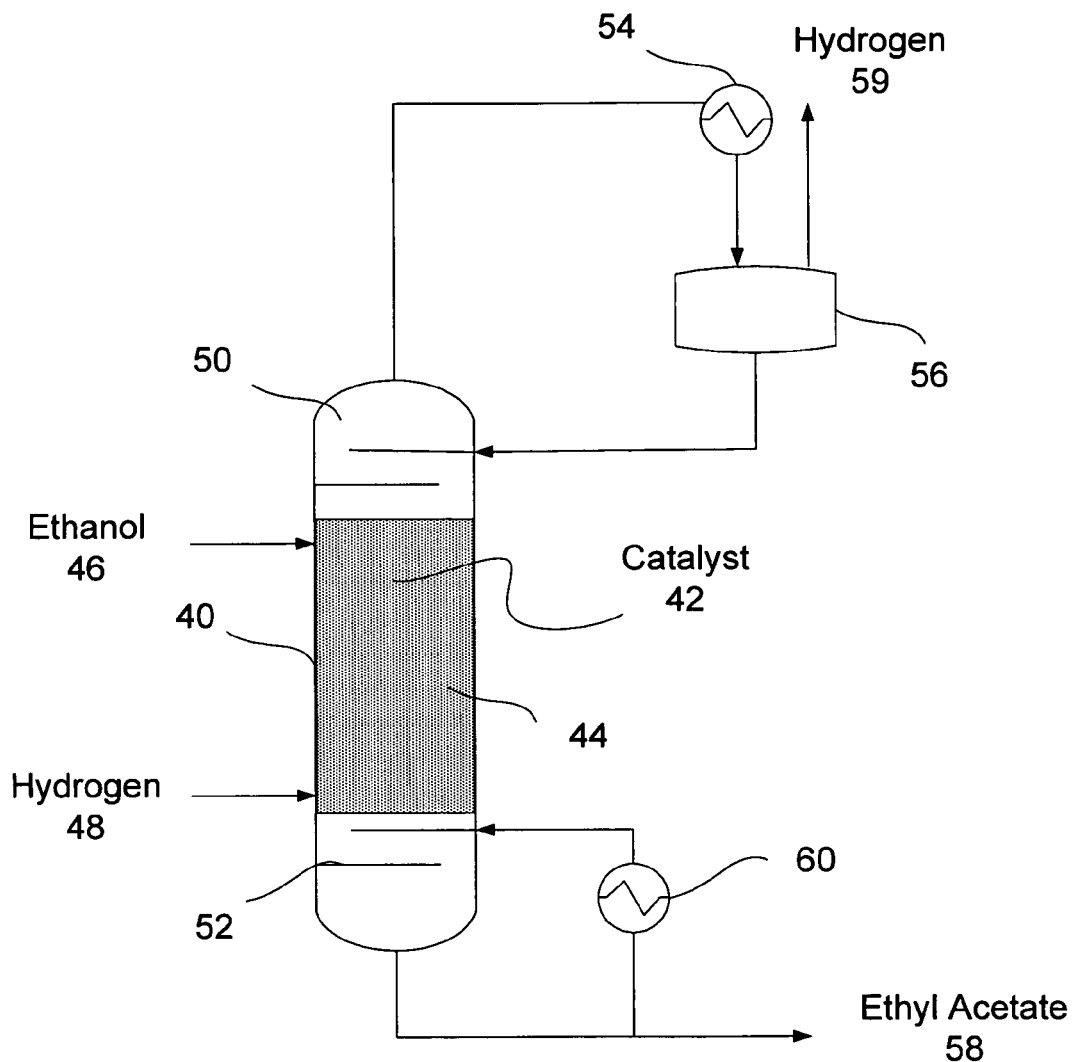
Figure 5: Double feed reactive distillation column schematic with an upper feed of ethanol and lower feed of hydrogen.

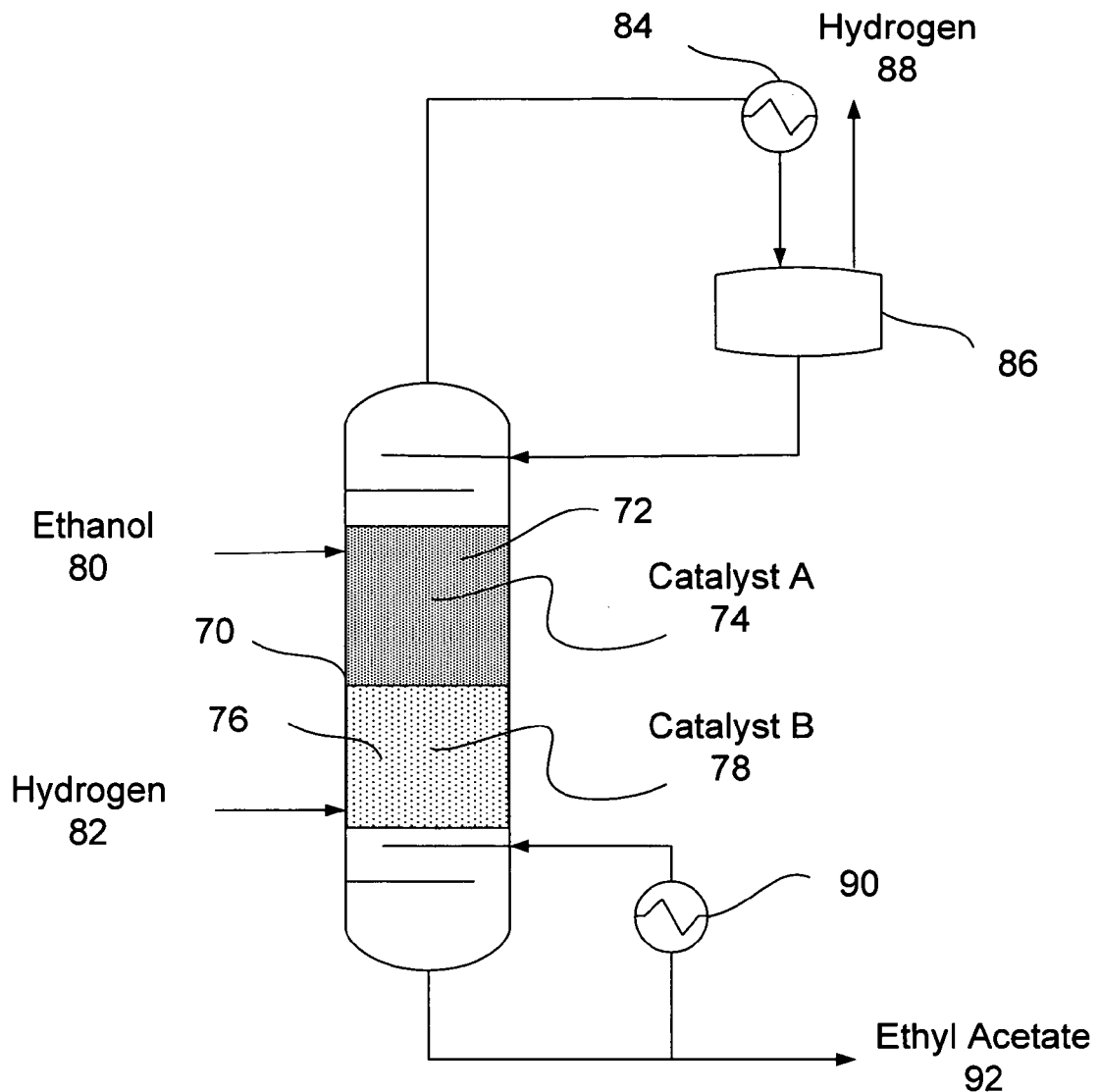
Figure 6: Double feed reactive distillation column schematic using dual catalyst beds with an upper feed of ethanol and lower feed of hydrogen.

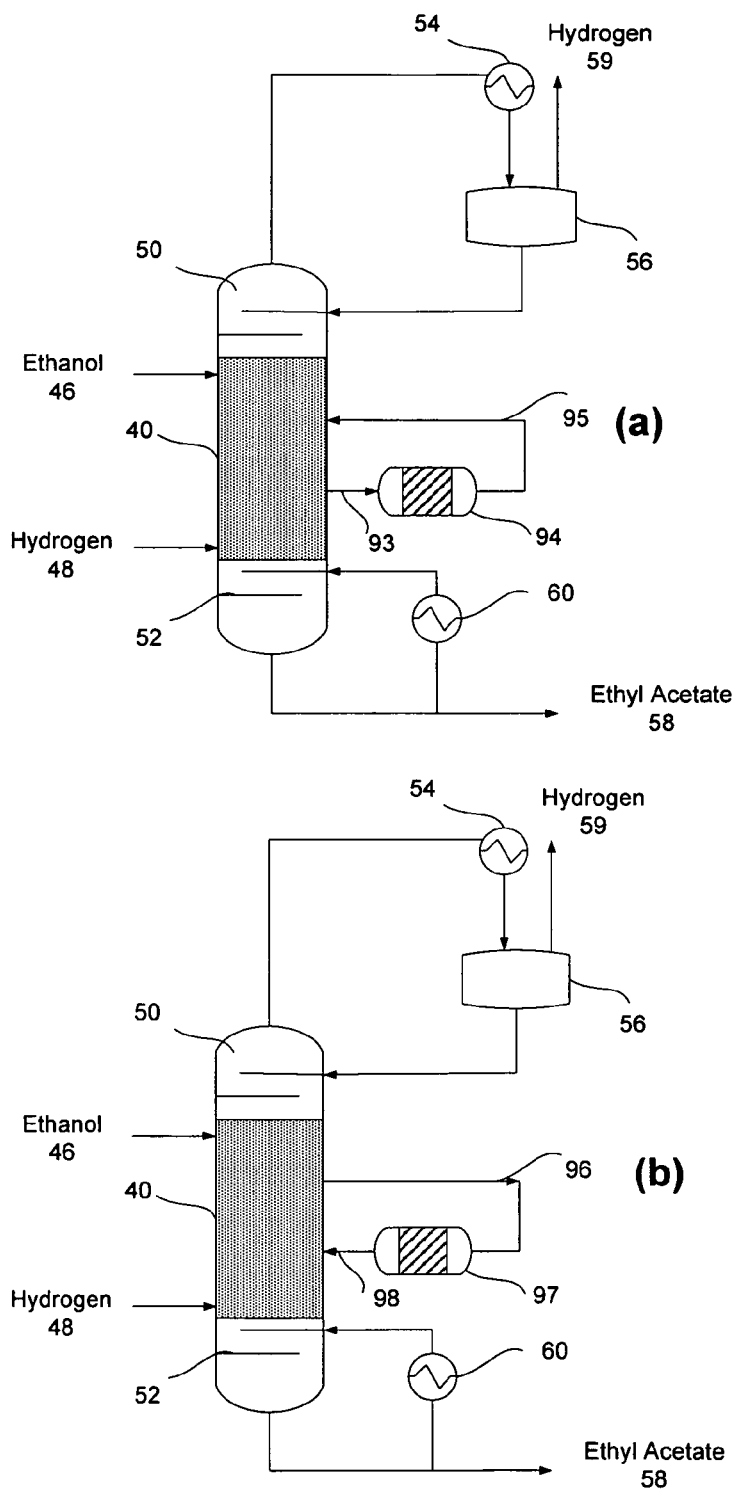
Figure 7: Side reactor configuration (a) upward flow feed to side reactor (b) downward flow feed to side reactor.

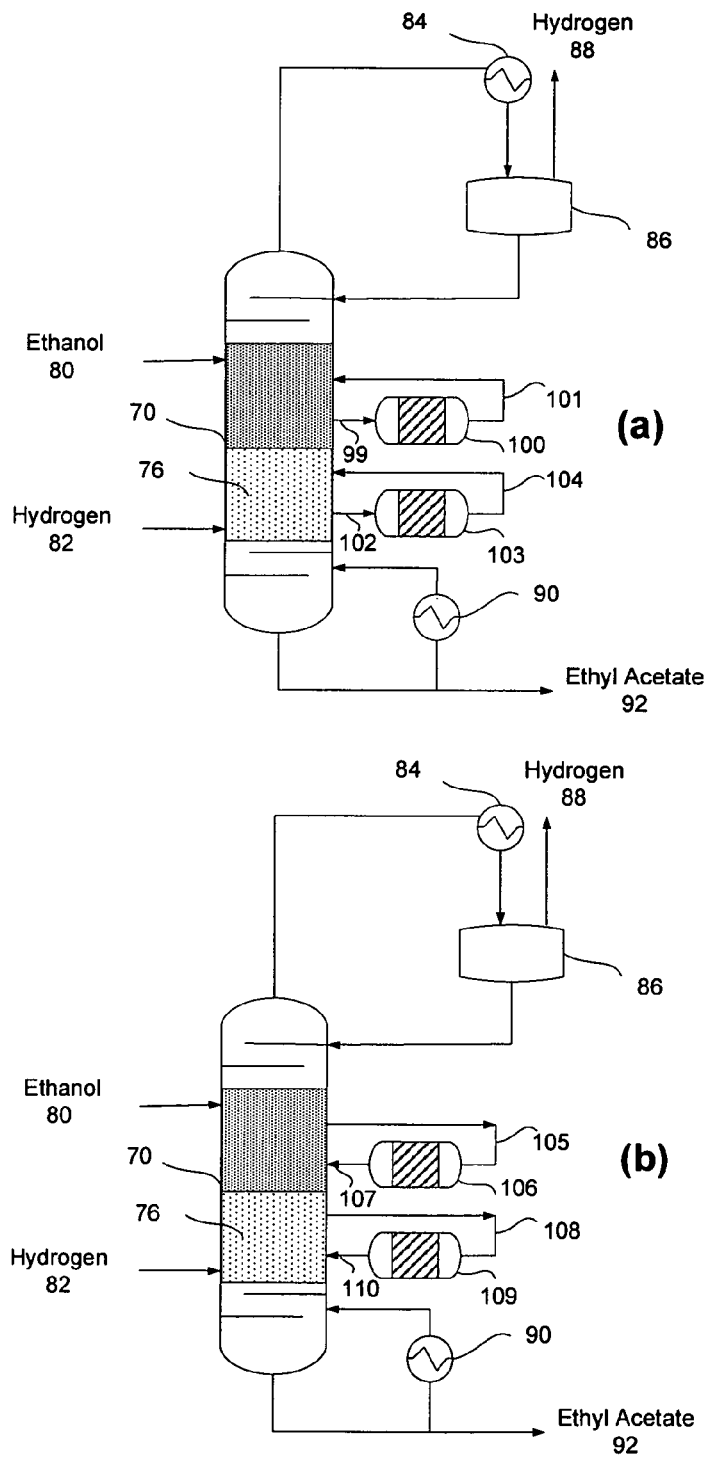
Figure 8: Double Side reactor configuration (a) upward flow feed to multiple side reactors (b) downward flow feed to multiple side reactors.

ETHYL ACETATE PRODUCTION

RELATED APPLICATIONS

This application claims the benefit of Gadewar, U.S. Prov Appl 61/253,349, filed Oct. 20, 2009, which is incorporated herein by reference in its entirety, including drawings.

FIELD OF THE INVENTION

The present invention relates to preparation of ethyl acetate by reactive distillation.

BACKGROUND OF THE INVENTION

The following discussion is provided solely to assist the understanding of the reader, and does not constitute an admission that any of the information discussed or references cited constitute prior art to the present invention.

Ethyl acetate can be produced from acetaldehyde according to the Tischenko reaction:

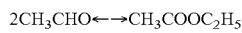
$$2CH_3CHO \leftarrow \rightarrow CH_3COOC_2H_5$$

When acetaldehyde is produced from ethanol, ethyl acetate can be produced from ethanol according to the following reaction:

$$2C_2H_5OH \leftarrow \rightarrow CH_3COOC_2H_5 + 2H_2$$

Alternately, ethanol can react with acetaldehyde according to the following reaction:

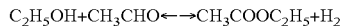
$$C_2H_5OH + CH_3CHO \leftarrow \rightarrow CH_3COOC_2H_5 + H_2$$

Conversion of primary alcohols into esters and ketones using copper catalyst is described by K. Takeshita in the Bulletin of the Chemical Society of Japan, (1978) vol. 51(9), pp 2622-2627.

U.S. Pat. No. 4,996,007 describes a process for the oxidation of primary alcohols to aldehydes, esters and acids. A primary alcohol is reacted with oxygen, with a catalyst selected from ruthenium, rhodium, platinum, palladium, rhenium and mixtures thereof, with the option of quaternary C1 to C20 alkyl ammonium co-catalyst, and dihydrodihydroxynaphthalene, dihydroxyanthracene or a mixture thereof as an oxygen activator.

In U.S. Pat. No. 4,220,803 catalytic dehydrogenation of ethanol for the production of acetaldehyde and acetic acid using a supported copper oxide essentially free of barium is proposed.

U.S. Pat. No. 4,052,424 suggested a silver-cadmium alloy catalyst for use in production of alkyl alkanoate esters, by contacting a primary alkanol in the vapor phase with the catalyst at a temperature of between about 250° C. and 600° C.

In U.S. Pat. No. 4,440,946 there is described a process for producing a carboxylate ester which comprises contacting a mixture of alcohol and aldehyde in the vapor phase with a co-precipitate composition comprising silver-cadmium-zinc-zirconium which is substantially in the free metal form.

Use of the Tischenko reaction for the production of mixed esters from aldehydes is described in U.S. Pat. No. 3,714,236.

U.S. Pat. No. 5,334,751 describes production of ethyl acetate by reaction of ethanol and oxygen in the presence of a solid catalyst that contains crystalline $TiP_2O_7$ and has the formula $Pd_aM_bTiPcO_7$, where M is Cd, Au, Zn, Tl, or an alkali metal or alkaline earth metal, a is 0.0005-0.2, b is 0.3a, c is 0.5-2.5, x has a value to satisfy the valencies, and Ti and P of the crystalline $TiP_2O_7$ represent part of the crystalline $TiP_2O_7$.

BR-A-91/04652 describes pre-treatment of a palladium on a silica carrier catalyst for production of ethyl acetate by direct oxidation of ethanol with air.

Production of esters from primary alcohols by dehydrogenation using bromous acid or a salt thereof in acid medium is described in JP-A-59/025334.

In SU-A-362814 there is described a process for production of ethyl acetate by dehydrogenation of ethanol at 180° C. to 300° C. in the presence of a copper catalyst containing zinc as an activator with an ethanol feed rate of 250 to 700 liters per liter of catalyst per hour.

The dehydrogenation of ethanol to form ethyl acetate is described in GB-A-287846. This proposes use of a dehydrogenating agent, such as a copper catalyst, a temperature of from 250° C. to 500° C., and a pressure of more than 10 atmospheres (1.013×106 Pa).

Vapor phase contact of ethanol at a temperature above its critical temperature with a catalyst comprising copper and a difficulty reducible oxide, such as zinc oxide or manganese oxide, is proposed in GB-A-312345, use of a temperature of 375° C. and a pressure of 4000 psi (27.58 Mpa) being suggested.

GB-A-470773 teaches a process for conversion of ethanol to ethyl acetate by dehydrogenating ethanol over a catalyst consisting of a reduced metal, for example, copper on infusorial earth with 10% uranium oxide as promoter, maintained at a temperature of 220° C. to 260° C., removing by condensation some of the gas-vapor product rich in hydrogen resulting from the reaction, and returning the gaseous remainder rich in hydrogen to the catalyzing zone.

EP-A-0151886 describes a process for the preparation of C2+ esters of alkyl carboxylic acids from C2+ primary alcohols which comprises contacting a vaporous mixture containing a primary C2+ alkanol and hydrogen in an alkanol:hydrogen molar ratio of from 1:10 to about 1000:1 at a combined partial pressure of alkanol and hydrogen of from about 0.1 bar (103 Pa) up to about 40 bar ($4 \times 10^6$ Pa) and at a temperature in the range of from about 180° C. to about 300° C. in a catalytic reaction zone with a catalyst consisting essentially of a reduced mixture of copper oxide and zinc oxide, and recovering a reaction product mixture containing a primary C2+ alkyl ester of an alkyl carboxylic acid which ester contains twice as many carbon atoms as the primary C2+ alkanol.

In EP-A-0201105 there is described a method for converting primary alcohols, such as ethanol, to their corresponding alkanoate esters which involves the regulation of the mole feed ratio of hydrogen gas to alkanol in the reaction zone of a copper-chromite containing catalyst.

One method of separating ethyl acetate from ethanol and water involves extractive distillation with an extractive agent comprising polyethylene glycol and dipropylene glycol, diethylene glycol, or triethylene glycol as described in U.S. Pat. No. 4,569,726 or with an extractive agent containing dimethyl sulphoxide as described in U.S. Pat. No. 4,379,028.

Separation of ethyl acetate from a composition comprising ethyl acetate, ethanol and water is described in JP-A-05/186392 by feeding the composition to a distillation column to obtain a quasi-azeotropic mixture comprising ethyl acetate, ethanol and water, condensing it, separating the condensate into an organic layer and an aqueous layer, returning the organic layer to the column, and recovering ethyl acetate as a bottom product from the column.

EP-A-0331021 describes how carbonylation of olefins to produce monocarboxylate esters causes formation of aldehydes and acetals as byproducts. Monocarboxylate esters produced in this way are subjected to a three step purification process involving treatment with a strongly acidic agent, followed by hydrogenation and distillation. The initial treatment with a strongly acidic agent is intended to convert acetals to vinyl ethers and aldehydes and acetals to aldols. The subsequent hydrogenation step then converts these compounds to byproducts which are more easily separated from the desired monocarboxylate ester.

EP-A-0101910 contains a similar disclosure regarding carbonylation of olefins to give monocarboxylate esters. It proposes treatment of the monocarboxylate ester with hydrogen at elevated temperature in the presence of an acidic ion exchanger or zeolite doped with one or more metals of Group VIII of the Periodic Table, followed by hydrogenation. It is stated that acetals present as byproducts are converted to vinyl ethers which are converted by hydrogenation to low boiling esters or the aldehydes and acetals are converted to high boilers by an aldol reaction. Unsaturated ketones are converted to saturated ketones.

U.S. Pat. No. 4,435,595 describes the use of reactive distillation to produce high-purity methyl acetate, by esterifying methanol and acetic acid. The process provides for the use of acetic acid and methanol which flow in counter-current through a single reactive distillation column in the presence of an acid catalyst. The acetic acid, in addition to being a reagent, also acts as an extracting agent for the non-reacted methanol and for the water which has been produced. Therefore, the methyl acetate is separated continuously from the acetic acid and removed from the top of the column.

SUMMARY OF THE INVENTION

Current commercial methods for producing ethyl acetate present limitations in such areas as system complexity, the need for expensive prior syntheses, difficult product separations, and/or overall cost. The present invention addresses these limitations by providing a reactive distillation system in which ethanol is the sole or primary feed. In some embodiments, the ethanol feed is used in conjunction with a separate second feed of hydrogen.

Thus, the present invention provides a process (and corresponding system) for the production of ethyl acetate from ethanol which includes reacting ethanol over a suitable dehydrogenation catalyst in a reactive distillation column, thereby producing ethyl acetate and hydrogen. Preferably a single reactive distillation column is used. Hydrogen gas is removed (preferably continuously) from the top of the reactive distillation column as a top product. Ethyl acetate is removed (preferably continuously) from the bottom of the column as a liquid bottoms product.

Optionally but advantageously, contaminating byproducts present following reaction of the ethanol over the dehydrogenation catalyst can be reacted over a suitable hydrogenation catalyst in the lower part of the column or in a separate hydrogenation reactor. The hydrogenation can convert difficult to separate byproducts into species which are easier to separate from the ethyl acetate. Consequently, the process can also include purifying the ethyl acetate by distilling out resulting hydrogenated byproducts.

Thus, as indicated above, a first aspect of the invention concerns a reactive distillation process producing high purity ethyl acetate from ethanol, where the process involves dehydrogenating ethanol over a dehydrogenation catalyst in a reactive distillation column. Ethyl acetate is removed during the distillation process as a liquid bottoms product and hydrogen is removed during the distillation process as a gaseous top product.

In certain embodiments, the process also include hydrogenating contaminants or reaction byproducts in the liquid bottoms product or in the reacted fluid after is has passed over the dehydrogenation catalyst and separating the hydrogenated contaminants or byproducts from the ethyl acetate.

Some implementations of the process utilize a single feed of ethanol; the reactive distillation column contains a generally central dehydrogenation catalyst zone and the single feed of ethanol is delivered into the column above or near the top of the catalyst zone; the reactive distillation column contains a generally central dehydrogenation catalyst zone and the single feed of ethanol is delivered into the column below or near the bottom of the catalyst zone.

In particular embodiments, the process also includes passing reaction fluid, after it has passed over the dehydrogenation catalyst, through a hydrogenation reactor which includes a hydrogenation catalyst, e.g., such that n-butyraldehyde and/or butan-2-one, if present, are hydrogenated; the hydrogenation catalyst may, for example, include metals and/or oxides of nickel, palladium, platinum, ruthenium, iron, molybdenum and/or mixtures thereof as catalyst material, e.g., on a support material such as carbon, alumina, silica, chromia, and/or titania; bottoms product is separated in a separation column which receives product from the hydrogenation reactor, separating, for example, n-butanol and 2-butanol from ethyl acetate.

Some implementations of the process utilize dual feeds of ethanol and hydrogen fed to the reactive distillation column, where the ethanol feed is above the hydrogen feed. In many cases the reactive distillation column includes a dehydrogenation catalyst zone and the ethanol feed is above or near the top of that dehydrogenation catalyst zone (or alternatively within the dehydrogenation catalyst zone, e.g., within the upper $3/4$, $2/3$, $1/2$, $1/3$, or $1/4$ of the dehydrogenation catalyst zone) and the hydrogen feed is below or near the bottom of the dehydrogenation catalyst zone. The reactive distillation column can advantageously also include a hydrogenation catalyst zone below the dehydrogenation catalyst zone; usually the hydrogen feed is below or near the bottom of that hydrogenation catalyst zone.

For many embodiments in which dual feeds of ethanol and hydrogen are used, the molar ratio of Ethanol:Hydrogen for the dual feeds is from 1:10 to 1000:1, e.g., from 1:10 to 1:1, 1:1 to 5:1, 1:1 to 10:1, 5:1 to 25:1, 5:1 to 50:1, 10:1 to 50:1, 10:1 to 100:1, 50:1 to 200:1, 50:1 to 400:1, 100:1 to 500:1, 100:1 to 1000:1, 200:1 to 1000:1, or 500:1 to 1000:1.

For any of the column configurations used in the present invention, in certain embodiments, the reactive distillation is performed at a pressure from 1 bar to 50 bar, e.g., 1 to 5, 5 to 10, 7 to 12, 13 to 15, 13 to 20, 15 to 20, 15 to 30, 20 to 30, 20 to 50, 30 to 40, 30 to 50, or 40 to 50 bar; the reactive distillation is performed at a pressure where ethanol-ethyl acetate azeotrope is not present; the number of stages or the number of height equivalents of a theoretical plate (HETP) is from 2 to 100, e.g., from 2 to 10, 10 to 20, 10 to 50, 20 to 30, 20 to 70, 30 to 40, 30 to 50, 30 to 100, 50 to 70, 50 to 100, or 70 to 100; the high purity ethyl acetate contains at least 95, 96, 97, 98, 99, or 99.5% ethyl acetate by weight.

In the present process, a number of different catalysts can be used for the dehydrogenation, e.g., where the dehydrogenation catalyst includes a catalyst material such as metals and/or oxides of copper, ruthenium, rhodium, platinum, palladium, rhenium, silver, cadmium, zinc, gold, thallium, manganese, aluminum, chromium, nickel, iron, molybdenum and/or mixtures thereof, in most cases on a support such as carbon, alumina, silica, chromia, and/or titania. Such catalysts are useful for either the single feed or dual feed processes specified in embodiments above.

A related aspect of the invention concerns a reactive distillation system, e.g., as indicated in the preceding aspect. Thus, the invention also provides a reactive distillation system for producing high purity ethyl acetate from ethanol. The system includes a reactive distillation column which includes a dehydrogenation catalyst (usually located generally centrally or at intermediate level in the column), an ethanol feed which feeds ethanol into the column such that it passes over the dehydrogenation catalyst, a top product gaseous hydrogen removal passage, and a bottoms product liquid ethyl acetate removal passage.

In certain advantageous embodiments, the system also includes a hydrogenation catalyst positioned to contact liquid product following passage over the dehydrogenation catalyst, generally with a hydrogen feed located prior to or at the hydrogenation catalyst.

In some embodiments, the chemical feed to the reactive distillation column is a single ethanol feed; the reactive distillation column contains a generally central dehydrogenation catalyst zone and the single ethanol feed is delivered into the column above or near the top of that catalyst zone; the reactive distillation column contains a generally central dehydrogenation catalyst zone and the single ethanol feed is delivered into the column below or near the bottom of that catalyst zone.

In certain embodiments, the system also include a hydrogenation catalyst which hydrogenates contaminants or reaction byproducts in the liquid bottoms product or in the reacted fluid after is has passed over the dehydrogenation catalyst and separating the hydrogenated contaminants or byproducts from the ethyl acetate. The hydrogenation catalyst may be in the same column as the dehydrogenation catalyst or in a separate hydrogenation reactor.

Some embodiments of the system incorporate a single feed of ethanol into the reactive distillation column; the reactive distillation column contains a dehydrogenation catalyst zone (often generally central) and the single feed of ethanol is delivered into the column above or near the top of the catalyst zone; the reactive distillation column contains a generally central dehydrogenation catalyst zone and the single feed of ethanol is delivered into the column below or near the bottom of the catalyst zone.

In further embodiments, the system also includes a hydrogenation catalyst, e.g., in a hydrogenation reactor, over which reaction fluid (together with hydrogen) is passed after it has passed over the dehydrogenation catalyst; the reaction fluid, hydrogen, and hydrogenation catalyst are configured such that n-butyraldehyde and/or butan-2-one, if present, are hydrogenated, highly preferably without significantly hydrogenating ethyl acetate in the reaction fluid; the hydrogenation catalyst includes metals and/or oxides of nickel, palladium, platinum, ruthenium, iron, molybdenum and/or mixtures thereof as catalyst material, e.g., on a support material such as carbon, alumina, silica, chromia, and/or titania; bottoms product is separated in a separation column which receives product from the hydrogenation reactor, separating, for example, n-butanol and 2-butanol from ethyl acetate.

Some of the present systems incorporate dual feeds of ethanol and hydrogen fed to the reactive distillation column, where the ethanol feed is above the hydrogen feed. Thus, in many cases the reactive distillation column includes a dehydrogenation catalyst zone and the ethanol feed is above or near the top of that dehydrogenation catalyst zone (or alternatively within the dehydrogenation catalyst zone, e.g., within the upper ¾, ⅔, ½, ⅓, or ¼ of the dehydrogenation catalyst zone) and the hydrogen feed is below or within the dehydrogenation catalyst zone but below the ethanol feed, e.g., near the bottom of the dehydrogenation catalyst zone.

The reactive distillation column can advantageously also include a hydrogenation catalyst zone below the dehydrogenation catalyst zone; usually the hydrogen feed is below or within that hydrogenation catalyst zone, e.g., near the bottom of the hydrogenation catalyst zone.

For many embodiments in which dual feeds of ethanol and hydrogen are used, the molar ratio of Ethanol:Hydrogen for the dual feeds is from 1:10 to 1000:1, e.g., from 1:10 to 1:1, 1:1 to 5:1, 1:1 to 10:1, 5:1 to 25:1, 5:1 to 50:1, 10:1 to 50:1, 10:1 to 100:1, 50:1 to 200:1, 50:1 to 400:1, 100:1 to 500:1, 100:1 to 1000:1, 200:1 to 1000:1, or 500:1 to 1000:1.

For any of the column configurations used in the present invention, in certain embodiments, the reactive distillation is performed at a pressure from 1 bar to 50 bar, e.g., 1 to 5, 5 to 10, 7 to 12, 13 to 15, 13 to 20, 15 to 20, 15 to 30, 20 to 30, 20 to 50, 30 to 40, 30 to 50, or 40 to 50 bar; the reactive distillation is performed at a pressure where ethanol-ethyl acetate is not present; the number of stages or the number of height equivalents of a theoretical plate (HETP) is from 2 to 100, e.g., from 2 to 10, 10 to 20, 10 to 50, 20 to 30, 20 to 70, 30 to 40, 30 to 50, 30 to 100, 50 to 70, 50 to 100, or 70 to 100; the high purity ethyl acetate contains at least 95, 96, 97, 98, 99, or 99.5% ethyl acetate by weight.

In the present system, a number of different catalysts can be used for the dehydrogenation, e.g., where the dehydrogenation catalyst includes a catalyst material such as metals and/or oxides of copper, ruthenium, rhodium, platinum, palladium, rhenium, silver, cadmium, zinc, gold, thallium, manganese, aluminum, chromium, nickel, iron, molybdenum and/or mixtures thereof, in most cases on a support such as carbon, alumina, silica, chromia, and/or titania. Such catalysts are useful for either the single feed or dual feed processes specified in embodiments above.

In some embodiments of the process, side reactors, usually external side reactors, can be used with the reactive distillation column, e.g., to increase the residence time for reaction. The feed to the side reactors is liquid for top-down flow and vapor for bottom-up flow. One or more side reactors can be used.

The term "reactive distillation column" is used conventionally to refer to a distillation column in which both reaction and separation is performed. In this case, the primary and desired reaction is the conversion of two ethanol molecules to one ethyl acetate molecule with release of two hydrogen molecules.

Reference to a "single feed" to a reactive distillation column means that the column has only one chemical feed stream supplying intended reactant(s) to the column. Nonetheless, such a single feed distillation column may have recycling feed streams where a part of the reactant liquid is drawn from the column and fed back into the column at a different point or a partial distillate is fed back into the column at a different point, e.g., to achieve improved separation and/or more complete reaction. A "single ethanol feed" thus refers to a single feed stream, in which ethanol is the sole or at least the primary constituent.

In contrast, the term "dual feed" in the context of a distillation column refers to two separate chemical feed streams. For example, in some of the present embodiments, dual feeds are an ethanol feed and a separate hydrogen feed.

Additional embodiments will be apparent from the Detailed Description and from the claims.

BRIEF DESCRIPTION OF THE DRAWINGS

FIG. 1 shows reactive residue maps for conversion of ethanol to ethyl acetate at pressures of 1 and 5 atmospheres (atm).

FIG. 2 shows reactive residue maps for conversion of ethanol to ethyl acetate at pressures of 10 and 20 atm.

FIG. 3 shows a simplified schematic of a reactive distillation system for catalytic conversion of ethanol to ethyl acetate using a single ethanol feed and a single catalyst.

FIG. 4 shows a simplified schematic of a reactive distillation system for catalytic conversion of ethanol to ethyl acetate using a single ethanol feed and a single catalyst, but with a hydrogenation reactor for the bottoms product from the reactive distillation column.

FIG. 5 shows a simplified schematic of a reactive distillation system for catalytic conversion of ethanol to ethyl acetate using dual feeds of ethanol (top) and hydrogen (bottom) with a single catalyst.

FIG. 6 shows a simplified schematic of a reactive distillation system for catalytic conversion of ethanol to ethyl acetate using dual feeds of ethanol (top) and hydrogen (bottom) with an upper dehydrogenation catalyst and a lower hydrogenation catalyst.

FIG. 7 shows a simplified schematics of side reactor reactive distillation columns using dual feeds of ethanol (top) and hydrogen (bottom) with a single catalyst (a) upward flow feed to side reactor (b) downward flow feed to side reactor.

FIG. 8 shows a simplified schematics of side reactor reactive distillation columns using dual feeds of ethanol (top) and hydrogen (bottom)) with an upper dehydrogenation catalyst and a lower hydrogenation catalyst (a) upward flow feed to side reactor (b) downward flow feed to side reactor.

DETAILED DESCRIPTION OF THE PREFERRED EMBODIMENTS

The present invention concerns a reactive distillation process for producing high purity ethyl acetate from ethanol. This process is highly beneficial as it provides an improved commercial method of upgrading ethanol to ethyl acetate, a more valuable product. This improved commercial process is particularly desirable and advantageous where there is an over-capacity for ethanol. Further, this process obviates the need for a separate acetaldehyde or acetic acid plant to provide precursors for the ethyl acetate production process. These advantages are provided in a process which can also be less expensive than those in the art for ethyl acetate production from ethanol.

Additionally the invention can provide a route to ethyl acetate by dehydrogenation of ethanol which is capable to yielding high purity ethyl acetate from ethanol feed streams containing significant amounts of impurities. One particular problem in production of ethyl acetate by dehydrogenation of ethanol is that the reaction product mixture is commonly a complex mixture including esters, alcohols, aldehydes and ketones. From a distillative separation point of view, the mixture is further complicated due to the presence of azeotropes. The reaction product mixtures commonly contain components with boiling points close to ethyl acetate (such as n-butyraldehyde and butan-2-one), including components which can form azeotropes with ethyl acetate, and/or other components of the mixture. This is a particular problem when high purity ethyl acetate is desired.

In conventional chemical processing, chemical reaction and the purification of the desired products by distillation are usually carried out sequentially. In many cases, the performance of this classic chemical process structure can be significantly improved by integration of reaction and distillation in a single multifunctional process unit. This integration concept is called 'reactive distillation'. As advantages of this integration, chemical equilibrium limitations can be overcome, higher selectivities can be achieved, the heat of reaction can be used in situ for distillation, auxiliary solvents can be avoided, and azeotropic or closely boiling mixtures can be more easily separated. Increased process efficiency and reduction in overall capital costs are the direct results of this approach.

Thus, as indicated above, the present invention provides a novel process for production of ethyl acetate from ethanol at a relatively low cost, along with a plant or distillation system with significantly reduced complexity using reactive distillation. The invention further provides an improved process for the production of high purity ethyl acetate from ethanol, or from a feedstock comprising a major proportion of ethanol and a minor proportion of impurities such as iso-propanol and iso-butanol. While not commonly present in ethanol feed streams, impurities which could poison the particular catalyst used should be avoided or removed. For example, sulfur or nitrogen heterocyclic compounds can frequently act as catalyst poisons and, if present, should be removed before introducing the ethanol feed stream to the reactive distillation column.

Ethyl acetate can be produced from ethanol according to the following reactions:

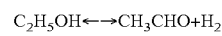

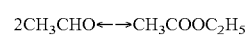

In the present process, ethanol reacts in a single continuous reactive distillation column which provides sufficient residence time to achieve high conversion of ethanol. Table 1 shows the effect of pressure on the boiling point of the pure components and azeotrope in the mixture. The azeotrope between ethanol and ethyl acetate disappears above a pressure of 13 atm.

TABLE 1

Boiling point of reaction components.

| | Boiling Point, C. | | | | | |
|---|---|---|---|---|---|---|
| | P = 1 atm | P = 5 atm | P = 10 atm | P = 20 atm | P = 30 atm | P = 40 atm |
| Hydrogen | −161 | −137.6 | −123.7 | −106.5 | −94.3 | −84.5 |
| Acetaldehyde | 20.4 | 71.9 | 101.1 | 136.4 | 160.7 | 180 |
| Ethanol | 78.3 | 125.2 | 150.2 | 179 | 198 | 212.7 |
| Ethyl acetate | 77 | 136 | 169.6 | 210.3 | 238.4 | 260.7 |
| Ethanol/Ethyl acetate azeotrope | 71.7 | 123.5 | 150.1 | No Azeo | No Azeo | No Azeo |

Residue curve maps can be used to indicate feasible product compositions for distillation columns. In the presence of reaction along with separation, reactive residue curve maps can be used to determine feasible products from a reactive distillation column. Reactive residue curve maps at a pressure of 1 atm and 5 atm respectively are shown in FIG. 1. The stable nodes in the diagram are ethanol and ethyl acetate, and, therefore, it is possible to design a reactive distillation column where either ethanol or ethyl acetate can be obtained as the bottoms product. Hydrogen is an unstable node in the diagram and can be obtained as the distillate. Acetaldehyde and the ethanol/ethyl acetate azeotrope are saddle points in the diagram.

Reactive residue curve maps at pressures of 10 atm and 20 atm respectively are shown in FIG. 2. The reactive residue curve map for any pressure above 20 atm is essentially identical to the reactive residue curve map at 20 atm.

In view of the reactive residue maps discussed above, a set of reactive distillation systems effective to produce high purity ethyl acetate from ethanol have been designed. The reactive distillation column can have single or multiple feed locations.

Reactive Distillation Column Configurations

As indicated above, the reactive distillation column is configured for the dehydrogenation of ethanol with the formation of ethyl acetate. The reaction is accomplished by passing the ethanol feed stream over a dehydrogenation catalyst under conditions where ethyl acetate is formed and hydrogen and ethyl acetate are withdrawn as top and bottoms products respectively. Such product draws drive the thermodynamics of the process toward the desired products. As one example of a useful reactive distillation column, a reactive distillation column with a single feed of ethanol as shown schematically in FIG. 3 can produce hydrogen as a distillate and ethyl acetate as a bottoms product. Column 10 contains a generally central catalyst zone 12, and usually will include a top stage or non-reactive rectifying section 13 and a bottom state or non-reactive stripping section 15. Ethanol feed 14 is commonly fed to the middle part of the reactive distillation column. Distillate removed at the top of the column is passed through a partial condenser 16, and hydrogen is separated from lower boiling constituents in reflux tank 18. The condensed lower boiling constituents (i.e., reflux) can be cycled back to the column for further reaction and/or separation. Bottoms product can be passed through reboiler 20, where a portion of the bottoms product is evaporated and added back to the bottom of the column. The column reflux and reboil ratios are maintained such that essentially pure ethyl acetate is obtained as the bottoms product. Ethyl acetate and hydrogen are produced due to the reaction over the dehydrogenation catalyst. Acetaldehyde may also be produced during the reaction if the conversion of acetaldehyde to ethyl acetate is incomplete.

Examples of useful catalysts for the reaction can include metals and/or oxides of copper, ruthenium, rhodium, platinum, palladium, rhenium, silver, cadmium, zinc, gold, thallium, manganese, aluminum, chromium, nickel, iron, molybdenum, and mixtures thereof. In many cases, the catalyst material will be supported, e.g., on carbon, alumina, silica, chromia or titania.

During operation, the reactants and products flow through the reactor/column reacting and flashing along the length of the reactor/column. The removal of hydrogen product, by flashing, preferentially to the other components along the reactive distillation column increases the extent of reaction. Also, hydrogen concentration increases from the middle part of the column towards the top of the column. At pressures of about 13 bar or lower, as ethyl acetate is formed from the reactants, azeotrope between ethyl acetate and ethanol occurs. The vapor product leaving the top of the reactive distillation column may contain ethanol and acetaldehyde in addition to hydrogen.

A partial condenser 16 allows hydrogen to be removed as a distillate, while acetaldehyde and ethanol is recycled back to the top of the reactive distillation column. As noted, the ethyl acetate and ethanol azeotrope disappears above a pressure of 13 atm, which improves the operation of the reactive distillation column. The column can be operated between a pressure of about 1 atm and about 50 atm. The temperature profile in the column is dictated by the mixture boiling point along the height of the column. High conversion of ethanol to products can be achieved by the counter-current flow of reactants and products in addition to overcoming the reaction equilibrium by removal of products.

Aldehydes and ketones such as n-butyraldehyde and butan-2-one may be produced in the reaction. These byproducts boil at temperatures close to the boiling point of ethyl acetate and may be difficult to separate from ethyl acetate. FIG. 4 shows a process schematic where the bottoms product from the reactive distillation column illustrated in FIG. 3 is sent to a hydrogenation reactor 24 containing a hydrogenation catalyst 26 with a hydrogen co-feed 28. A suitable catalyst may comprise metals and/or oxides of nickel, palladium, platinum, ruthenium, iron, molybdenum, supported on carbon, alumina, silica, chromia or titania. The n-butyraldehyde and butan-2-one impurities are hydrogenated and can then be separated using a distillation column. The outlet of the hydrogenation reactor may be cooled in condenser 30 before entering the distillation column 32. Ethyl acetate 36 with a purity of greater than 99% by weight can be obtained as the bottoms product of the distillation column. Unconverted hydrogen and the hydrogenated byproducts are removed as a distillate 34, e.g., to be used as fuel. This distillation column is operated between a pressure of 1 atm and 50 atm.

In another embodiment of the invention, the reactive distillation column has two feeds. Ethanol is fed to the upper part of the column (upper feed). Hydrogen is fed to the lower part of the column (lower feed). A schematic for the double feed reactive distillation column is shown in FIG. 5. This system includes column 40 containing catalyst 42 in catalyst zone 44, and commonly will include a top stage or non-reactive rectifying section 50 and a bottom state or non-reactive stripping section 52. In the illustrated system, ethanol feed 46 is delivered at or near the top of the catalyst zone 44, and the hydrogen feed 48 is delivered at or near the bottom of catalyst zone 44. It should be recognized columns can be designed with the ethanol feed location in other locations, e.g., within the catalyst zone but above the hydrogen feed, such as from the approximate middle of the catalyst zone to the top of the column. Similarly, columns with the hydrogen feed in other locations can also be designed, e.g., with the hydrogen feed from the approximate middle of the catalyst zone to the bottom of the column or even higher within the catalyst zone but below the ethanol feed. Highly preferably the ethanol and hydrogen feeds are separated sufficiently to allow byproduct hydrogenation to be substantially completed before hydrogen from the feed reaches substantial concentrations of ethanol being dehydrogenated. Ethanol reacts over the catalyst producing ethyl acetate and hydrogen. Examples of catalysts may include metals and/or oxides of copper, ruthenium, rhodium, platinum, palladium, rhenium, silver, cadmium, zinc, gold, thallium, manganese, aluminum, chromium, nickel, iron, molybdenum, and mixtures thereof, supported, e.g., on carbon, alumina, silica, chromia or titania. Due to boiling point difference, hydrogen moves towards the top of the column and ethyl acetate moves towards the bottom of the column. Acetaldehyde may be produced during the reaction and moves up in the column, and can be condensed in partial condenser 54, passed through reflux tank 56 and recycled back to the reaction zone. A part of the bottom draw is taken out as the ethyl acetate product stream 58, while the remaining part is passed through reboiler 60 to be recycled to the column. Hydrogen product 59 is taken out as distillate from the reflux tank 56. The stream passing through the reboiler provides the evaporation effect needed to operate the column.

Byproducts such as n-butyraldehyde and butan-2-one produced in the reaction boil close to ethyl acetate. The lower hydrogen feed is useful in hydrogenating the by-products to produce components that can be separated easily from ethyl acetate. The ratio of the hydrogen feed to the ethanol feed can beneficially be adjusted to minimize the amount of close boiling byproducts, while not excessively reducing ethyl acetate to ethanol. Hydrogen product from the reaction leaves at the top of the column. The column is operated between a pressure of about 1 atm and about 50 atm.

As schematically illustrated in FIG. 6, the reactive distillation column 70 has two feeds and uses two distinct catalyst zones, identified as an upper zone 72 containing Catalyst A 74 and a lower catalyst zone 76 containing Catalyst B 78. Ethanol feed 80 is fed to the upper part of the column (upper feed). Hydrogen feed 82 is fed to the lower part of the column (lower feed). Ethanol reacts over the upper catalyst (Catalyst A) producing ethyl acetate and hydrogen. Examples of catalysts may include metals and/or oxides of copper, ruthenium, rhodium, platinum, palladium, rhenium, silver, cadmium, zinc, gold, thallium, manganese, aluminum, chromium, nickel, iron, molybdenum, and mixtures thereof, supported, e.g., on carbon, alumina, silica, chromia or titania. As with previous schematic designs shown, the column will usually include a top stage or non-reactive rectifying section 71 and a bottom state or non-reactive stripping section 79.

Due to boiling point differences, hydrogen moves towards the top of the column and ethyl acetate moves towards the bottom of the column. Acetaldehyde may be produced during the reaction and moves up in the column, and can be condensed in condenser 84 and recycled back to the reaction zone through reflux tank 86. Byproducts such as n-butyraldehyde and butan-2-one produced in the reaction boil close to ethyl acetate. The lower hydrogen feed is useful in hydrogenating the by-products over the lower catalyst (Catalyst B) to produce components that can be separated easily from ethyl acetate. Examples of hydrogenation catalysts (Catalyst B) may comprise metals and/or oxides of nickel, palladium, platinum, ruthenium, iron, molybdenum, and/or mixtures thereof supported, e.g., on carbon, alumina, silica, chromia or titania. Hydrogen product from the reaction leaves at the top of the column. Subsequent purification of ethyl acetate may be needed to remove the hydrogenated byproducts from ethyl acetate, e.g., using a distillation column such as that as shown in FIG. 4 as distillation column 32. The column is operated between a pressure of about 1 atm and about 50 atm.

In the dual feed systems described above, the hydrogen feed should be at a sufficiently low level that it does not significantly adversely affect the dehydrogenation of ethanol in the zone above, while being effective to hydrogenate the undesirable close boiling point byproducts. Feed rates of hydrogen can be adjusted empirically to optimize this balance. Commonly, the ratio of product mixture:hydrogen will be in a range of about 500:1 to 1:1 molar ratio, more commonly about 500:1 to 10:1 or 500:1 to 100:1.

Side reactors connected to a reactive distillation column increases the catalyst holdup for improved reactant conversion. In the side reactor concept the reactor feed is withdrawn from the distillation column and the reactor effluent is returned back to the same column. The adequate catalyst amount is more easily arranged in a side reactor system where traditional reactor types and catalyst structures can be used. Also, the reaction conditions within the side reactor such as temperature can be adjusted independently of those prevailing in the distillation column by appropriate heat exchange.

Schematics for a side reactor reactive distillation column with a single catalyst are shown in FIG. 7. A single side reactor is shown, however, multiple side reactors along the length of the reactive distillation column can be used. FIG. 7 (*a*) shows a configuration where the feed 93 to the side reactor is bottom up and vapor phase. The outlet from side reactor 94 is stream 95 which is sent back to the distillation column at any location in the column above the location of feed 93. FIG. 7 (*b*) shows a configuration where the feed 96 to the side reactor is top down and liquid phase. The outlet from side reactor 97 is stream 98 which is sent back to the distillation column at any location in the column below the location of feed 96. The side reactors 94 and 97 each contain catalyst for converting ethanol into ethyl acetate. Examples of catalysts may include metals and/or oxides of copper, ruthenium, rhodium, platinum, palladium, rhenium, silver, cadmium, zinc, gold, thallium, manganese, aluminum, chromium, nickel, iron, molybdenum, and mixtures thereof, supported, e.g., on carbon, alumina, silica, chromia or titania.

Schematics for a side reactor reactive distillation with two feeds and using two distinct catalyst zones are shown in FIG. 8. A single side reactor is shown for each catalyst zone in the reactive distillation column, however, multiple side reactors along the length of the reactive distillation column can be used for each catalyst zone. FIG. 8 (*a*) shows a configuration where the top zone feed 99 to the side reactor 100 is bottom up and vapor phase. The bottom zone feed 102 to another side reactor 103 is also bottom up and vapor phase. The outlet from side reactor 100 is stream 101 which is sent back to the distillation column at any location in the column above the location of feed 99. The outlet from side reactor 103 is stream 104 which is sent back to the distillation column at any location in the column above the location of feed 102. FIG. 8 (*b*) shows a configuration where the top zone feed 105 to the side reactor 106 is top down and liquid phase. The bottom zone feed 108 to another side reactor 109 is also top down and liquid phase. The outlet from side reactor 106 is stream 107 which is sent back to the distillation column at any location in the column below the location of feed 105. The outlet from side reactor 109 is stream 110 which is sent back to the distillation column at any location in the column below the location of feed 108. Examples of catalysts for side reactors 100 and 106 may include metals and/or oxides of copper, ruthenium, rhodium, platinum, palladium, rhenium, silver, cadmium, zinc, gold, thallium, manganese, aluminum, chromium, nickel, iron, molybdenum, and mixtures thereof, supported, e.g., on carbon, alumina, silica, chromia or titania. Examples of hydrogenation catalysts for side reactors 103 and 109 may comprise metals and/or oxides of nickel, palladium, platinum, ruthenium, iron, molybdenum, and mixtures thereof supported, e.g., on carbon, alumina, silica, chromia or titania.

Production of Methyl Formate from Methanol

In addition to use of the systems and methods described herein for converting ethanol to ethyl acetate, those systems can also be used in processes with methanol as a feed instead of ethanol, with the production of methyl formate and H2 as products according to the following formula:

$$2CH_3OH \leftrightarrow HCOOCH_3 + 2H_2$$

Such a system and method can utilize selections from the catalysts indicated for use with the ethanol feed. Products can be withdrawn in similar manner as described for the ethanol to ethyl acetate process.

EXAMPLES

Example 1

Production of Ethyl Acetate from Ethanol

A 10 cm diameter distillation column is used, which has been rendered adiabatic by heating casings with temperatures controlled in such a way that the temperature gradient in the column is reproduced. Over a height of 3.5 m, the column is comprised of rectification zone with 8 stages each with a catalytic cell consisting of a cylindrical container with a flat bottom. The bottom of the container is equipped with a grid for retaining the catalyst and also can act as a gas and liquid distributor. The stripping zone is comprised of 12 stages, also with catalyst-containing cells. The rectification section is considered to be above the feed stage and the stripping section is considered to be below the feed stage. Each catalyst cell contains 5 wt % copper oxide on silica. 200 proof ethanol is fed to the 13$^{th}$ stage of the column, starting from the bottom.

The column is regulated by establishing a reflux ratio which is equal to 2.5 and controlling the base temperature to 211° C. and the absolute pressure to 20 bar. The reflux stream is mostly ethanol with small amounts of acetaldehyde. Under stabilized conditions, a bottoms stream and a distillate stream are collected with respective throughputs of about 170 g/h and 4 g/h. The bottoms product gives ethyl acetate purity of 98.5% with small amounts of n-butyraldehyde and butan-2-one.

Example 2

Selective Hydrogenation of n-butyraldehyde and butan-2-one

Selective hydrogenation of n-butyraldehyde and butan-2-one in the presence of ethyl acetate was conducted over a hydrogenation catalyst. The reactor was filled with 20 g of 0.1 wt % Pd on silica catalyst. Before the selective hydrogenation reaction, the catalyst was reduced at a temperature of 250° C. for 30 minutes. The catalyst reduction was conducted at atmospheric pressure by delivering hydrogen using a mass flow controller. At the end of this procedure the catalyst was fully reduced.

The bottoms product from the reactive distillation column whose composition is given in Table 2 was introduced to a heater at a rate of 30 g/h and mixed with hydrogen prior to admission to the selective hydrogenation reactor. The reaction product was cooled using a jacketed condenser and the liquid condensate was analyzed by gas chromatography. The results are summarized in Table 2, showing n-butyraldehyde and butan-2-one reduced to trace levels.

TABLE 2

Hydrogenation Feed and Products
Temperature 250° C.
Pressure 20 atm

| Component | Weight % | |
|---|---|---|
| | Feed | Products |
| Ethyl acetate | 93 | 92.9 |
| Ethanol | 2 | 2.1 |
| Iso-propanol | 3 | 3 |
| n-butyraldehyde | 1.5 | trace |
| butan-2-one | 0.5 | trace |
| 2-butanol | 0 | 0.48 |
| n-butanol | 0 | 1.52 |

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values or value range endpoints are provided for embodiments, additional embodiments are described by taking any 2 different values as the endpoints of a range or by taking two different range endpoints from specified ranges as the endpoints of an additional range. Such ranges are also within the scope of the described invention. Further, specification of a numerical range including values greater than one includes specific description of each integer value within that range.

Thus, additional embodiments are within the scope of the invention and within the following claims.

What is claimed is:

1. A reactive distillation process producing high purity ethyl acetate from ethanol, comprising:
    feeding a feed stream comprising ethanol to a reactive distillation column;
    contacting the ethanol with a catalyst within the reactive distillation column, wherein the catalyst is disposed in the reactive distillation column;
    dehydrogenating ethanol over the catalyst in the reactive distillation column in the liquid phase;
    removing ethyl acetate during the distillation process as a liquid bottoms product; and
    removing hydrogen during the distillation process as a gaseous top product.

2. The reactive distillation process of claim 1, further comprising hydrogenating contaminants in said liquid bottoms product and separating the hydrogenated contaminants from said ethyl acetate.

3. The reactive distillation process of claim 1, wherein said high purity ethyl acetate comprises at least 98% ethyl acetate.

4. The reactive distillation process of claim 1, wherein the feed stream comprising ethanol is the only feed stream fed to the reactive distillation column.

5. The reactive distillation process of claim 4, wherein said reactive distillation column contains a generally central dehydrogenation catalyst zone and said single feed stream comprising ethanol is delivered into said column above or near the top of said catalyst zone.

6. The reactive distillation process of claim 4, wherein said reactive distillation column contains a generally central dehydrogenation catalyst zone and said single feed stream comprising ethanol is delivered into said column below or within said catalyst zone.

7. The reactive distillation process of claim 6, wherein said dehydrogenation catalyst comprises a catalyst material selected from the group consisting of metals and/or oxides of copper, ruthenium, rhodium, platinum, palladium, rhenium, silver, cadmium, zinc, gold, thallium, manganese, aluminum, chromium, nickel, iron, molybdenum, zirconium, and mixtures thereof.

8. The reactive distillation process of claim 7, wherein said catalyst material is on a support selected from the group consisting of carbon, alumina, silica, chromic, and titania.

9. The reactive distillation process of claim 4, wherein a hydrogenation reactor comprising a hydrogenation catalyst is located downstream of the reactive distillation column, and wherein the process further comprises: receiving the liquid bottoms stream at the hydrogenation reactor, and hydrogenating n-butyraldehyde and butan-2-one, if present, in the hydrogenation reactor.

10. The reactive distillation process of claim 9, wherein said hydrogenation catalyst comprises a catalyst material selected from the group consisting of metals and/or oxides of nickel, palladium, platinum, ruthenium, iron, molybdenum, and mixtures thereof.

11. The reactive distillation process of claim 10, wherein said catalyst material is supported on a support material selected from the group consisting of carbon, alumina, silica, chromic and titania.

12. The reactive distillation process of claim 9, further comprising a separation column which receives product from said hydrogenation reactor, wherein n-butanol and 2-butanol are separated from ethyl acetate.

13. The reactive distillation process of claim 1, further comprising feeding a second feed stream comprising hydrogen to the reactive distillation column, and wherein the feed stream comprising ethanol is fed to the reactive distillation column above the second feed stream comprising hydrogen.

14. The reactive distillation process of claim 13, wherein said reactive distillation column comprises a dehydrogenation catalyst zone and said feed stream comprising ethanol is fed to the reactive distillation column above or near the top of said dehydrogenation catalyst zone and said second feed stream comprising hydrogen is fed to the reactive distillation column below or near the bottom of said dehydrogenation catalyst zone.

15. The reactive distillation process of claim 13, wherein the molar ratio of Ethanol:Hydrogen for the dual feed is from 1:10 to 1000:1.

16. The reactive distillation process of claim 1, wherein said reactive distillation is performed at a pressure from 1 bar to 50 bar.

17. The reactive distillation process of claim 1, wherein the number of stages or the number of height equivalents of a theoretical plate (HETP) is from 2 to 100.

18. A reactive distillation process producing high purity ethyl acetate from ethanol, comprising:
  feeding a first feed stream comprising ethanol and a second feed stream comprising hydrogen to a reactive distillation column, wherein the first feed stream is fed to the reactive distillation column at a point above the second feed stream, wherein the reactive distillation column comprises:
    a dehydrogenation catalyst zone, wherein the first feed stream is above or near the top of said dehydrogenation catalyst zone, and
    a hydrogenation catalyst zone below the dehydrogenation catalyst zone, wherein the second feed stream is below, near the bottom of, or within said hydrogenation catalyst zone;
  dehydrogenating ethanol over a dehydrogenation catalyst in the dehydrogenation catalyst zone during a distillation process to produce ethyl acetate and hydrogen,
  removing the ethyl acetate during the distillation process as a liquid bottoms product; and
  removing the hydrogen during the distillation process as a gaseous top product.

19. The reactive distillation process of claim 18, wherein dehydrogenating ethanol over the dehydrogenation catalyst further produces by-products, and wherein the reactive distillation process further comprises:
  hydrogenating at least a portion of the by-products over a hydrogenation catalyst in the hydrogenation catalyst zone to produce hydrogenated by-products.

20. The reactive distillation process of claim 19, further comprising:
  separating ethyl acetate from the hydrogenated by-products.

* * * * *